(12) United States Patent
Ionescu-Zanetti et al.

(10) Patent No.: US 10,167,502 B2
(45) Date of Patent: Jan. 1, 2019

(54) MOLECULAR CHARACTERIZATION OF SINGLE CELLS AND CELL POPULATIONS FOR NON-INVASIVE DIAGNOSTICS

(71) Applicant: Fluxion Biosciences, Inc., South San Francisco, CA (US)

(72) Inventors: Cristian Ionescu-Zanetti, Berkeley, CA (US); Jeff Jensen, San Francisco, CA (US); Michael Schwartz, Oakland, CA (US)

(73) Assignee: Fluxion Biosciences, Inc., Alameda, CA (US)

( * ) Notice: Subject to any disclaimer, the term of this patent is extended or adjusted under 35 U.S.C. 154(b) by 378 days.

(21) Appl. No.: 15/086,592

(22) Filed: Mar. 31, 2016

(65) Prior Publication Data

US 2016/0289754 A1 Oct. 6, 2016

Related U.S. Application Data

(60) Provisional application No. 62/142,663, filed on Apr. 3, 2015.

(51) Int. Cl.
*B01L 3/00* (2006.01)
*C12Q 1/6869* (2018.01)
*C12Q 1/6806* (2018.01)

(52) U.S. Cl.
CPC ......... *C12Q 1/6869* (2013.01); *C12Q 1/6806* (2013.01)

(58) Field of Classification Search
CPC ........................................................ B01L 3/00
See application file for complete search history.

(56) References Cited

U.S. PATENT DOCUMENTS 3,970,518 A 7/1976 Giaever
4,157,323 A 6/1979 Yen et al.
(Continued)

FOREIGN PATENT DOCUMENTS

EP 0708331 A1 4/1996
EP 1448771 B1 8/2004
(Continued)

OTHER PUBLICATIONS

Lee et al., Separation of model mixtures of epsilon-globin positive fetal nucleated red blood cells and anucleate erythrocytes using a microfluidic device, J Chromatogr A. Mar. 12, 2010;1217(11):1862-6. doi: 10.1016/j.chroma.2010.01.065. Epub Jan. 25, 2010.*
(Continued)

*Primary Examiner* — Aaron A Priest
(74) *Attorney, Agent, or Firm* — Asif Ghias

(57) ABSTRACT

The invention discloses diagnostic techniques based on single cell genomics, consisting of obtaining a blood sample, enriching a sub-population of cells present in the blood sample, sequestering individual cells or group of cells from the blood sample, obtaining sequencing data from the sequestered cells or group of cells, using genetic variant information to determine the provenance of the cells, and genetically analyzing the cells of the correct provenance to provide a diagnostic readout. Using the cell-based testing techniques of the invention, the number of false positives is greatly reduced when compared to cell-free DNA (cfDNA) based traditional testing techniques. The invention may be effectively employed for non-invasive prenatal (NIPT) diagnostics, oncological testing and other diagnostic procedures.

4 Claims, 5 Drawing Sheets

(56) References Cited

U.S. PATENT DOCUMENTS

| | | |
|---|---|---|
| 4,219,411 A | 8/1980 | Yen et al. |
| 4,710,472 A | 12/1987 | Saur et al. |
| 5,053,344 A | 10/1991 | Zborowski |
| 5,409,813 A | 4/1995 | Schwartz |
| 5,508,164 A | 4/1996 | Kausch et al. |
| 5,602,042 A | 2/1997 | Farber |
| 5,744,366 A | 4/1998 | Kricka et al. |
| 5,763,203 A | 6/1998 | Ugelstad et al. |
| 5,795,470 A | 8/1998 | Wang et al. |
| 5,837,200 A | 11/1998 | Diessel et al. |
| 5,842,787 A | 12/1998 | Kopf-sill et al. |
| 5,885,470 A | 3/1999 | Parce et al. |
| 5,942,443 A | 8/1999 | Parce et al. |
| 5,972,721 A | 10/1999 | Bruno et al. |
| 6,068,752 A | 5/2000 | Dubrow et al. |
| 6,153,073 A | 11/2000 | Dubrow et al. |
| 6,187,270 B1 | 2/2001 | Schmitt et al. |
| 6,238,538 B1 | 5/2001 | Parce et al. |
| 6,251,343 B1 | 6/2001 | Dubrow et al. |
| 6,274,337 B1 | 8/2001 | Parce et al. |
| 6,315,940 B1 | 11/2001 | Nisch et al. |
| 6,403,348 B1 | 6/2002 | Rubinsky et al. |
| 6,413,782 B1 | 7/2002 | Parce et al. |
| 6,429,025 B1 | 8/2002 | Parce et al. |
| 6,432,630 B1 | 8/2002 | Blankenstein |
| 6,437,551 B1 | 8/2002 | Krulevitch et al. |
| 6,454,945 B1 | 9/2002 | Weigl et al. |
| 6,479,299 B1 | 11/2002 | Parce et al. |
| 6,540,895 B1 | 4/2003 | Spence et al. |
| 6,562,604 B2 | 5/2003 | Rubinsky et al. |
| 6,589,729 B2 | 7/2003 | Chan et al. |
| 6,592,821 B1 | 7/2003 | Wada et al. |
| 6,632,619 B1 | 10/2003 | Harrison et al. |
| 6,653,089 B2 | 11/2003 | Takayama et al. |
| 6,686,184 B1 | 2/2004 | Anderson et al. |
| 6,686,193 B2 | 2/2004 | Maher et al. |
| 6,699,697 B2 | 3/2004 | Klemic et al. |
| 6,742,661 B1 | 6/2004 | Schulte et al. |
| 6,759,191 B2 | 7/2004 | Farinas et al. |
| 6,770,434 B2 | 8/2004 | Shvets et al. |
| 6,776,896 B1 | 8/2004 | Osipchuk |
| 6,899,800 B2 | 5/2005 | Osipchuk et al. |
| 6,900,021 B1 | 5/2005 | Harrison et al. |
| 6,927,049 B2 | 8/2005 | Rubinsky et al. |
| 6,932,893 B2 | 8/2005 | Bech et al. |
| 6,936,462 B1 | 8/2005 | Owen et al. |
| 6,969,604 B1 | 11/2005 | Yakovenko |
| 6,979,553 B2 | 12/2005 | Farinas et al. |
| 6,989,089 B2 | 1/2006 | Nisch et al. |
| 7,013,739 B2 | 3/2006 | Schroeder et al. |
| 7,018,819 B2 | 3/2006 | Orwar et al. |
| 7,067,263 B2 | 6/2006 | Parce et al. |
| 7,112,433 B2 | 9/2006 | Tyvoll et al. |
| 7,122,301 B2 | 10/2006 | Shvets et al. |
| 7,138,269 B2 | 11/2006 | Blankenstein |
| 7,141,415 B2 | 11/2006 | Wirix-Speetjens |
| 7,176,016 B2 | 2/2007 | Maher et al. |
| 7,214,298 B2 | 5/2007 | Spence et al. |
| 7,221,455 B2 | 5/2007 | Chediak et al. |
| 7,241,565 B2 | 7/2007 | Bullen et al. |
| 7,244,349 B2 | 7/2007 | Vogel et al. |
| 7,288,785 B2 | 10/2007 | Vestergaard et al. |
| 7,312,085 B2 | 12/2007 | Chou et al. |
| 7,358,077 B2 | 4/2008 | Zimmermann et al. |
| 7,361,500 B2 | 4/2008 | Stett et al. |
| 7,390,650 B2 | 6/2008 | Karlsson et al. |
| 7,452,726 B2 | 11/2008 | Chou et al. |
| 7,470,518 B2 | 12/2008 | Chiu et al. |
| 7,563,614 B2 | 7/2009 | Orwar et al. |
| 8,058,056 B2 | 11/2011 | Lee et al. |
| 8,293,524 B2 | 10/2012 | Ionescu-Zanetti et al. |
| 2002/0039783 A1 | 4/2002 | McMillan |
| 2002/0045566 A1 | 4/2002 | Gribkoff et al. |
| 2002/0064841 A1 | 5/2002 | Klemic et al. |
| 2002/0125139 A1 | 9/2002 | Chow et al. |
| 2002/0164777 A1 | 11/2002 | Kelly et al. |
| 2002/0177238 A1 | 11/2002 | Karp et al. |
| 2002/0182627 A1 | 12/2002 | Wang et al. |
| 2002/0182642 A1 | 12/2002 | Orwar et al. |
| 2002/0195337 A1 | 12/2002 | Osipchuk et al. |
| 2003/0022268 A1 | 1/2003 | Lepple-Wienhues |
| 2003/0065452 A1 | 4/2003 | Hickman |
| 2003/0121778 A1 | 7/2003 | Dodgson et al. |
| 2003/0129581 A1 | 7/2003 | Owen et al. |
| 2003/0138767 A1 | 7/2003 | Bullen et al. |
| 2003/0139336 A1 | 7/2003 | Norwood et al. |
| 2003/0143720 A1 | 7/2003 | Hickman |
| 2003/0153067 A1 | 8/2003 | Stett et al. |
| 2003/0153076 A1 | 8/2003 | Villeponteau et al. |
| 2003/0159999 A1 | 8/2003 | Oakey et al. |
| 2003/0180965 A1 | 9/2003 | Yobas et al. |
| 2003/0199050 A1 | 10/2003 | Mangano et al. |
| 2003/0219884 A1 | 11/2003 | Lison et al. |
| 2003/0224531 A1 | 12/2003 | Brennen et al. |
| 2004/0005696 A1 | 1/2004 | Vesterguard et al. |
| 2004/0005901 A1 | 1/2004 | Ala-Luukko |
| 2004/0028567 A1 | 2/2004 | Parce et al. |
| 2004/0072278 A1 | 4/2004 | Chou et al. |
| 2004/0106126 A1 | 6/2004 | Fendler |
| 2004/0146849 A1 | 7/2004 | Huang et al. |
| 2004/0202994 A1 | 10/2004 | Timperman |
| 2004/0229349 A1 | 11/2004 | Daridon |
| 2004/0260204 A1 | 12/2004 | Boecker et al. |
| 2005/0009004 A1 | 1/2005 | Xu et al. |
| 2005/0026283 A1 | 2/2005 | Ormar et al. |
| 2005/0058990 A1 | 3/2005 | Guia et al. |
| 2005/0070018 A1 | 3/2005 | Johnson et al. |
| 2005/0118723 A1 | 6/2005 | Padmanabhan et al. |
| 2005/0129581 A1 | 6/2005 | McBride et al. |
| 2005/0170510 A1 | 8/2005 | Huang et al. |
| 2005/0196746 A1 | 9/2005 | Xu et al. |
| 2005/0224351 A1 | 10/2005 | Ungar et al. |
| 2005/0266478 A1 | 12/2005 | Huang et al. |
| 2005/0277125 A1 | 12/2005 | Benn et al. |
| 2006/0003310 A1 | 1/2006 | Klauke et al. |
| 2006/0006067 A1 | 1/2006 | Unger |
| 2006/0194255 A1 | 8/2006 | Finkel |
| 2006/0234298 A1 | 10/2006 | Chiu et al. |
| 2006/0269385 A1 | 11/2006 | Zobel et al. |
| 2006/0286549 A1 | 12/2006 | Sohn et al. |
| 2007/0155016 A1* | 7/2007 | Lee ............... B01L 3/502707 435/461 |
| 2007/0243523 A1 | 10/2007 | Ionescu Zanetti et al. |
| 2008/0050739 A1 | 2/2008 | Stoughton et al. |
| 2008/0160634 A1 | 7/2008 | Su et al. |
| 2008/0302732 A1 | 12/2008 | Soh et al. |
| 2009/0053799 A1 | 2/2009 | Chang-yen et al. |
| 2009/0117004 A1 | 5/2009 | Fritchie et al. |
| 2009/0209029 A1 | 8/2009 | Guia et al. |
| 2009/0220932 A1 | 9/2009 | Ingber et al. |
| 2009/0220979 A1 | 9/2009 | Davis et al. |
| 2009/0264298 A1 | 10/2009 | Lim et al. |
| 2009/0297327 A1 | 12/2009 | Zobel et al. |
| 2010/0159506 A1 | 6/2010 | Parikh et al. |
| 2010/0196897 A1 | 8/2010 | Manaresi et al. |
| 2010/0252436 A1 | 10/2010 | Park et al. |
| 2011/0117577 A1 | 5/2011 | Reboud et al. |
| 2013/0017538 A1 | 1/2013 | Ionescu-Zanetti et al. |
| 2014/0247971 A1* | 9/2014 | Bharadwaj ........ B01L 3/502761 382/133 |

FOREIGN PATENT DOCUMENTS

| | | |
|---|---|---|
| EP | 1597576 B1 | 11/2005 |
| EP | 2191895 B1 | 6/2010 |
| EP | 2792751 A1 | 10/2014 |
| GB | 2371626 A | 7/2002 |
| JP | 2004/097886 A | 4/2004 |
| JP | 2005/028201 A | 2/2005 |
| WO | 1998/052691 A1 | 11/1998 |
| WO | 1999/055827 A1 | 11/1999 |
| WO | 2002-101387 A2 | 12/2002 |
| WO | 2005/089253 A2 | 9/2005 |
| WO | 2007/008609 A2 | 1/2007 |

(56) References Cited

FOREIGN PATENT DOCUMENTS

| WO | 2007/024701 A2 | 3/2007 |
|---|---|---|
| WO | 2008/072029 A2 | 6/2008 |
| WO | 2009/008925 A2 | 1/2009 |
| WO | 2009/026566 A1 | 2/2009 |
| WO | 2009/076560 A2 | 6/2009 |
| WO | 2010/117458 A1 | 10/2010 |

OTHER PUBLICATIONS

Bhagat et al., Pinched flow coupled shear-modulated inertial microfluidics for high-throughput rare blood cell separation, Lab Chip. Jun. 7, 2011;11(11):1870-8. doi: 10.1039/c0lc00633e. Epub Apr. 19, 2011.*
Huang et al., A microfluidics approach for the isolation of nucleated red blood cells (NRBCs) from the peripheral blood of pregnant women, Prenat Diagn. Oct. 2008;28(10):892-9. doi: 10.1002/pd.2079.*
Narayanamurthy et al., Microfluidic hydrodynamic trapping for single cell analysis: mechanisms, methods and applications, Anal. Methods, 2017, 9, 3751-3772, May 12, 2017.*
PCT-US2016-025208_Fluxion_InternationalSearchReportAndWrittenOpinion dated Jul. 11, 2016.
Lu—Microfluidic Shear Devices for Quantitative Analysis of Cell Adhesion, Anal Chem, 2004_76:5257-5264.
Lundqvist—Altering the Biochemical State of Individual Cultured Cells, Proc Natl Acad Sci USA, 1998, 09_01;95 (18):10356-10360.
Matthews—Characterization of a Micromachined Planar Patch Clamp, 1st Intl IEEE-EMBS, Neural Eng Conf, 2003.
Melville—Direct Magnetic Separation of Red Cells from Whole Blood, Nature, 1975;255:706.
Nagrath—Isolation of Rare Circulating Tumor Cells in Cancer Patients by Microchip Technology, Nature, 2007, 12, 20;450(7173):1235-1239.
Needham—Electro-mechanical Permeabilization of Lipid Vesicles, Biophys J, 1989, 05;55(5):1001-1009.
Neubert—Patch Clamping Moves to Chips, Anal Chem, 2004, 09, 01;76(17):327A-330A.
Neumann—Gene Transfer into Mouse Ivoma Cells by Electroporation in High Electric Fields, EMBOJ, 1982;1 (7):841-845.
Neumann—Mechanism of Electroporative Dye Uptake by Mouse B Cells, Biophys J, 1998, 01;74(1):98-108.
Nolkrantz—Electroporation of Single Cells and Tissues, Analytical Chemistry, 2001, 73(18):4469-4477.
Pamme—Magnetism and Microlluidics, Lab on a Chip, 2006, 01,01;6(1):24.
Rae—Single-Cell Electroporation, Pflugers Arch Eur J Physiol 2, 2002, 2;443(4):664-670.
Safarik—Use of Magnetic Techniques for the (solution of Cells, Journal of Chromatography B:Biomedical Sciences and Applications, 1999;722:33-53.
Sakamann—Patch Clamp Techniques for Studying Ionic Channels, Annual Rev Physiol, 1984;46:455-472.
Schroeder—Ion Works-HT—A New High-throughput Electrophysiology, Journal of Biomolecular Screening, 2003, 8(1):50-64.
Seo—Integrated Multiple Patch-Clamp Array Chip Via Lateral Cell Trapping Junctions, Applied Physics Letters, 2004, 84(11):1973-1975.
Smistrup—Magnetic Separation in Microfluidic Systems UsingMicrofabricated, Journal of Magnetism and Magnetic Materials, 2005;293(1):597-604.
Steel—The Flow Thru Chip-A3-D Biochip Platform, Eaton Publishing, Mass, 2000, pp. 87-117.
Stett—Cytocentering—A Novel Technique Enabling Automated Cell-by-Cell Patch, Receptors Channels, 2003;9 (1):59-66.
Stett—Patch-Clamping of Primary Cardiac Cells with Micro-Openings, Med Biol Eng Comput, 2003, 03;41 (2):233-240.
Takayasu—Continuous Magnetic Separation of Blood Components from Whole Blood,Applied Superconductivity, IEEE Transactions, 2000, 03;10(1):927-930.

Takayasu—HGMS Studies of Blood Cell Behavior in Plasma, Magnetics, IEEE Transactions, 1982, 11;18 (6):1520-1522.
Thorsen, Microfluidic Large-Scale Integration, Science, 2002, 10, 18;298(5593):580-584.
Tibbe—Magnetic Field Design for Selecting and Aligning Immunomagnetic Labeled Cells, Cytometry, 2002, 02, 19;47 (3):163-172.
Trapani—Control of Ion Channel Expression for Patch Clamp Recordings, Bmc Neuroscience, 2003, 4:15.
Tsong—Electroporation of Cel IMembranes-QuoVadis?, Drug Discovery Today, 2001, 60:297-306.
Wang—Microfluidic Sorting of Mammalian Cells by Optical Force Switching, Nature Biotechnology, 2004, 12, 19;23(1):83-87.
Weaver—Decreased Bilayer Stability Due to Transmembrane Potentials, Phys Letters, 1981, 86A:57-59.
Weaver—Electroporation—A General Phenomenon for Manipulating Cells and Tissues, J Cell Biochem, 1993, 4;51(4):426-435.
Weaver—Theory of Electroporation—Electroporation and Electrofusion in Cell Biology, Plenum Press, 1989, pp. 111-126.
Whitesides—Magnetic Separations in Biotechnology, Trends in Biotechnologym 1983;1(5):144-148.
Xia—Combined Microfluidic-Micromagnetic Separation of Living Cells in Continuous Flow, Biomedical Microdevices, 2006, 12, 01;8(4):299-308.
Xu—Aptamer-Based Microfluidic Device for Enrichment Sorting and Detection of Multiple Cancer Cells, Analytical chemistry, 2009, 09, 01;81(17):7436-7422.
Xu—Ion-Channel Assay Technologies: Quo Vadis?, Drug Discovery Today, 2001, 6:1278-1287.
Yamada—Pinched Flow Fractionation: Continuous Size Separation of Particles Utilizing a Laminate Flow, Analytical Chemistry, 2004;76(18):5465-5471.
Yang—Optimization of an Enrichment Process for Circulating Tumor Cells from the Blood, Biotechnology and Bioengineering, 2009, 02, 01;102(2):521-534.
Zheng—3D Microfilter Device for Viable Circulating Tumor Cell (CTC) Enrichment from Blood, Biomedical Microdevices, 2010, 12, 27;13:203-213.
EP Appl No. 07759449.7—Examination Report dated Jan. 17, 2011.
EP Appl No. 12811159.8—EP Search Report dated Feb. 25, 2015.
PCT/US2005/008349—International Search Report dated Dec. 2, 2005.
PCT/US2007/065001—International Search Report dated Dec. 7, 2007.
PCT/US2012/29770—PCT International Search Repord dated Oct. 16, 2012.
PCT/US2012/29770—PCT Written Opinion dated Oct. 16, 2012.
U.S. Appl. No. 11/466,104—Amendment to Non-Final Office Action dated Jun. 25, 2009.
U.S. Appl. No. 11/466,104—Non-Final Office Action dated Jul. 23, 2010.
U.S. Appl. No. 11/466,104—Non-Final Office Action dated Jun. 25, 2009.
U.S. Appl. No. 11/690,831—Non-Final Office Action dated Feb. 25, 2010.
U.S. Appl. No. 60/404,886, filed Aug. 21, 2002, Orwar.
U.S. Appl. No. 60/710,305, filed Aug. 21, 2005, Ionescu-Zanetti.
U.S. Appl. No. 60/744,034 filed Mar. 31, 2006, Ionescu-Zanetti.
Abiror, 246—Electric Breakdown of Bilayer Lipid Membranes, Bioelectrochem, 1979, vol. (Issue) 6(1), pp. 37-52.
Ahn, A Fully Integrated Micromachined Magnetic Particle Separator, Journal of Microelectromechanical Systems, 1996, vol. (Issue) 5(3), pp. 151.
Akinlaja, The Breakdown of Cell Membranes, Biophys J,1998;75:247-254.
Amaxa-Biosystems, <http://www.amaxa.com/96-wellnucleofection.html>, accessed Jan. 8, 2008.
Ambion—The RNA Company-si Porter TM96 Electroporation Chamber—onweb, accessed Jan. 8, 2008.
Asmild—Upscaling and Automation of Electrophysiology, Receptors and Channels, 2003;9:49-58.
Ausubel—Current Protocols in Molecular Biology—vols. -I-II-III, John Wiley and Sons, 1997 (Table of Contents).

(56) References Cited

OTHER PUBLICATIONS

Ausubel—Short Protocols in Molecular Biology—A Compendium of Methods, John Wiley and Sons, 2002 (Table of Contents).
AXPORATOR800A—Molecular Devices <http://moleculardevices-com/pages/instruments/cn_axoporator800.html>, accessed Aug. 13, 2008.
Azevedo—Morphological Study of Saccharomyces cerevisiae Cells Treated with Magnetic Fluid, Magnetics,IEEE Transactions, 2003, 9;39(5):1660-2662.
Batzer—Enhanced Evolutionary PCR Using Oligonucleotides, Nucleic Acids Res, 1991, 19(18):5081.
Bennet—Trends in Ion Channel Drug Discovery, Trends Biotechnol, 2003, 21(12):563-569.
Bio-Rad-Com, <http://biorad-com/B2B/BioRad/product>, accessed Jan. 7, 2008.
Bonetta—Flow Cytometry Smaller and Better, Nature Methods, 2005, 2(10):785-795.
Bor—Magnetic Split-Flow Thin Fractionation New Technique for Separation, Journal of Chromatography A, 1998, 07 17;813(2):313-324.
Brown—Improvement to Parallel Plate Flow Chambers, BMC-Immunol, 2001.
BTX—Molecular Delivery Systems, <http://www.btxonline.com/products> accessed Jan. 7, 2008.
Burnett—FluorescenceImagingOfElectricallyStimultatedCells, J Biomol Screen, 2003, 12;8(6):660-667.
Chalmers—Flow-through Immunomagnetic Cell Separation, Biotechnology Progress, 1998, 02 06;14(1):141-148.
Chang—Guide to Electroporation and Electrofusion, Academic Press, 1992 (Table of Contents).
Deng—Fabrication of Magnetic Microfiltration Systems Using Soft Lithography, Applied Physics Letters, 2009;80(3):461-463.
Dove—Screening for Content—The Evolution of High Throughput, Nature Biotechnology, 2003;21:859-864.
Entzeroth—Emerging Trends in High-Throughput Screening, Current Opinion in Pharmacology, 2003;3:522-529.
Fertig—Activity of Single Ion Channel Proteins, Applied Physics Letters, 2002;81:4865-4867.
Fertig—Stable Integration of Isolated Cell Membrane Patches in a Nanomachined Aperture, Applied Physics Letters_2000;77:1218-1220.
Fertig—Whole Cell Patch Clamp Recording Performed on a Planar Glass Chip, Biophysical Journal, 2002;82:3056-3062.
Fiedler—Dielectrophoretic Sorting of Particles and Cells in a Microsystem, Analytical Chemistry, 1998;70(9):1909-1915.
Franzreb —Protein Purification Using Magnetic Absorbent Particles, Applied Microbiology and Biotechnology, 2006, 02, 23;70(5):505-516.
Fu—A Microfabricated Fluorescence-ActivatedCell Sorter, Nature Biotechnology, 1999;17(11):1109-1111.
Gill—Flux Assays in High Throughput Screening, Assay Drug Dev Technology, 2003, 10, 1(5):709-717.
Gleghorn—Capture of Circulating Tumor Cells from Whole Blood of Prostate Cancer Patients, Lab on a Chip, 2010, 01, 01;10(1):27.
Haas—Single-Cell Electroporation for Gene Transfer InVivo, Neuron, 2001,3:29(3):583-591.
Handgretinger—Isolation and Transplantation of Autologous Peripheral CD34+ Progenitor Cells, Bone Marrow Transplant, 1998, 05:987-993.
Hartig—Continuous Sorting of Magnetizable Particles by Means of Specific Deviation, Review of Scientific Instruments, 1995, 05;66(5):3289-3295.
Hirschbein—Magnetic Separations in Chemistry and Biochemistry, Chemtech, 1982;12:172-179.
Huang—Continuous Particle Separation Through Deterministic Lateral Displacement, Science, 2004;304 (5673):987-990.
Huang—Microfabricated Electroporation Chip for Single Cell Membrane Permeabilization, Sensors and Actuators A, 2001;89:242-249.
Hunt—Addressable Micropost Array for the Dielectrophoretic Manipulation of Particles in Fluid, Applied Physics Letters, 2004;85(26):6421.
Immke—Ion-Ion Interactions at the Selectivity Filter, Journal of Gen Physiology, 2000, 04;115(4):509-518.
Innis—PCR-Protocols—A Guide to Methods and Applications, Elsevier Science and Technology Books, 1990 (Table of Contents).
Ionescu-Zanetti—Mammalian Electrophysiology on a Microfluidic Platform, PNAS, 2005, 102(20):9112-9117.
Khine—A Single Cell Electroporation Chip, Lab Chip, 2005, 5:38-43.
Klemic—Micromolded PDMS-Planar Electrode Allows Patch Clamp, Biosensors and Bioelectronics, 2002;17:597-604.
Lee—Manipulation of Biological Cells Using a Microelectromagnet Matrix, Applied Physics Letters, 2004;85(6):1063.
Lehnert—Realization of Hollow-SiO2-Micronozzles for Electrical Measurments on Living Cells, Applied Phys Lett, 2002;81:5063-5065.
Lin—Structure Formation at TheInterface of Liquid-Liquid Bilayer, Macromolecules, 2002;35:3971-3976.
Li—Transport Manipulation and Reaction of Biological Cells On-Chip, Anal Chem,1997.
Lu—Microfabricated Device for Subcellular Organelle Sorting, Analytical Chemistry, 2004, 10;76(19):5705-5712.
U.S. Appl. No. 60/868,864, filed Dec. 6, 2006,Ionescu-Zanetti.

* cited by examiner

MOLECULAR CHARACTERIZATION OF SINGLE CELLS AND CELL POPULATIONS FOR NON-INVASIVE DIAGNOSTICS

RELATED APPLICATIONS

This application claims priority from U.S. Provisional Patent Application No. 62/142,663, filed on Apr. 3, 2015, which is incorporated herein by reference in its entirety.

FIELD OF THE INVENTION

This invention relates to the fields of non-invasive pre-natal testing (NIPT), single cell genomics based testing procedures, and non-invasive diagnostic testing in oncology.

BACKGROUND ART

Non-Invasive Pre-Natal Diagnostics

Non-invasive pre-natal diagnostics are a growing area of development, in part due to increasing parental age (and therefore genetic risk) and the presence of genetic abnormalities in a significant percentage of the infant population. The tests currently on the market, Ariosa, Verify and XX from Verinata, Natera and Sequenom respectively rely on the detection of key abnormalities via counts of molecules derived from different chromosomes in the blood of the pregnant mother, and enable detection of Trisomies 21, 18 and 13.

While these tests have gained relatively widespread market adoption, they are limited to being marketed as a 'screening' test due to their relatively low positive predictive value (PPV). As an example, one such screening test, when testing for Trisomy 18, has true positive rate of about 40 patients in 400 positive screening tests. That translates to about a 10% PPV. Because of the potential for false positives, a positive result using the non-invasive test needs to be followed up by an amniocentesis confirmatory test that has a much lower error rate (and higher PPV).

The high false positive rate (and difficulty in developing a true diagnostic) is due to the fact that fetal cell-free DNA (fcfDNA) is present in concentrations of only 4-12% as compared to the mother's cell-free DNA (cfDNA). Consequently, for a fetal trisomy (say Trisomy 18), if there are 3 as opposed to 2 copies of chromosome 18, the change in a sample that is 5% fetal DNA is only (5%/2)=2.5%. The copy number determination therefore needs to be very accurate, as data has a greater than 5% spread and statistical methods need to be employed to determine any imbalance while sequencing at a high depth of coverage. There are a number of different commercial tests based on cfDNA and this type of consideration.

While previous tests have been proposed based on fetal cells in the mother's blood, they have been hard to develop into commercial tests because of the variable cell number recovered and the relatively low concentration of fetal cells to maternal cells in the final sample. A number of different modalities have been used to separate fetal cells out using either posts in a microfluidic channel, macro scale immunomagnetic separation, size (Isolation by Size of Tumor cells i.e. ISET) or ferromagnetic properties of red blood cells. No one modality has demonstrated fetal cell purities of above 10% post enrichment, and thereby low purities have precluded commercial development. For a more thorough treatment of these and related topics, the reader is referred to U.S. Pat. Nos. 8,058,056, 8,293,524 and U.S. Patent Application Publication No. 2013/0017538 A1.

Single Cell Analysis

In areas unrelated to prenatal diagnostics, methods and devices have been proposed to enable the analysis of single cells. The simplest approach, termed Limiting Dilution, consists of measuring the concentration of cells in a certain volume, followed by mixing of the whole sample and dispensing a volume that is expected to contain a single cell in each of many wells. This has the limitation of resulting in 1 cell on average per well, and a distribution of 0, 1, and 2 cells with a few higher numbers, but where only about 60% of wells contain a single cell in optimized protocols. Another related approach is to utilize a fluorescence activated cell sorter (FACS) instrument in order to sort single cells directly into wells of a well plate. This approach suffers from some of the same limitations in success rate, and requires expensive equipment to perform.

A number of different approaches for isolating and analyzing single cells using microfluidic devices have also been proposed. One approach previously commercialized by Fluidigm, Inc. as part of their C1 product offering utilizes a trap within the flow of a microfluidic channel, and microchannel based valve-ing to isolate the cell and to perform lysis, followed by nucleic acid amplification and extraction for up to 96 cells.

One approach previously proposed for single cell immobilization was to use an array of lateral junctions. The approach provided for a method of either patch clamp recording or electroporation of single cells, which would lead to lysis, but did not clearly describe a method for further analyzing the resulting nucleic acids from single cells by performing the necessary amplification, sequestration and extraction of the amplified material. For a more rigorous treatment of this approach, the reader is referred to U.S. Pat. No. 8,058,056. The single cell immobilization methods described may also be followed up by microscopy based detection of chromosome abnormalities for each cell.

OBJECTS OF THE INVENTION

In view of the limitations of the prior art, it is an object of the invention to provide a non-invasive diagnostic method based on single cell genomics that results in significantly lower false positives as compared to the traditional techniques based on analyzing cfDNA of population of cells.

It is another object of the invention to provide a high-reliability and high-sensitivity testing protocol for NIPT, oncology and other diagnostic procedures, that has a much higher positive predictive value (PPV) than possible through the techniques of the prior art.

It is yet another object of the invention to provide for non-invasive, prenatal testing techniques that can produce highly accurate diagnostic readouts of aneuploidies and other genetic diseases of the fetus.

It is another object of the invention to provide for non-invasive testing techniques that can produce highly accurate diagnostic readouts to assist in prognostics and determination of treatment efficacy in oncology.

Still other objects and advantages of the invention will become apparent upon reading the detailed specification and reviewing the accompanying drawing figures.

SUMMARY OF THE INVENTION

The objects and advantages of the invention are secured by an apparatus and methods of performing diagnostics based on single cell genomics. The diagnostics techniques provided by the invention are well suited for Non-Invasive Pre-natal Testing (NIPT), oncological testing, or other diagnostics procedures.

A blood sample is first obtained from an expecting mother or a patient. Then a sub-population of cells from the blood sample is enriched to achieve a higher level of purity. The sub-population can be fetal cells for NIPT usage, or cancer cells for oncological testing. The enrichment process may employ a variety of techniques including immunomagnetic separation, microfluidic manipulation, cell morphology based separation, anti-body binding based separation, or other enrichment techniques available to a person of average skill. These techniques may be employed singly or in combination to achieve the desired levels of purity, ideally greater than or equal to 10% against the background.

After enrichment, individual cells or groups/subsets of cells of the sub-population are isolated/separated/sequestered. A number of techniques may be employed for cell separation or sequestration. These include trapping individual cells at junctions of microfluidic channels that have differing sizes. Preferably, cell trapping happens at channel junctions at the bottom of the wells of a well plate. Cell trapping usually occurs under the influence of negative pressure applied to the smaller channel of such a junction. Selective releasing and retrapping of cells can also be used to enrich certain cell populations based on morphology.

Once the cells have been trapped, a lysing solution is preferably applied to the trapped/immobilized cells. The lysing solution can be transported into the wells by pipetting or by using another microfluidic channel. Eventually, the lysed contents of the individual cell or groups of cells from the enriched sub-population are obtained in separate/isolated reservoirs or wells for further processing.

At this stage, various pressure manipulation techniques may be used around the microfluidic structures to minimize or cut off unwanted flow in selected channels. Now nucleic amplification of the cellular contents is preferably performed using a variety of available techniques, including Polymerase Chain Reaction (PCR) and Ligase Chain Reaction (LCR). Furthermore, individual cells may advantageously be barcoded in the reservoirs such that sequencing occurs only on barcoded cells.

At this point, sequencing is performed on the amplified (and preferably barcoded) lysed cells. The sequence data is obtained and recorded, based on which the provenance of the separated cells is determined. Cell provenance is preferably determined based on a genetic variant information, such a single nucleotide variant (SNV) information. Cell provenance may reveal that in the case of NIPT, the cell(s) is/are of maternal origin or of fetal origin. In the case of oncological testing, cell provenance may reveal that the cell(s) is/are normal i.e. of patient origin or of cancer/tumor origin. Cell provenance may alternatively be determined by identifying individual molecules of the cells by unique barcodes, and then applying a consensus operation.

Sequence data is also used to determine the genetic characteristics of the cells applicable for the particular diagnostics of interest. However the genetic characteristics only need to be determined for cells that have the correct origin i.e. fetal cells for NIPT, and tumor cells for oncology.

For NIPT, the fetal genetic characteristics may indicate the presence of an aneuploidy such as a particular trisomy, or the presence of another SNV related disorder such as an addition or a deletion of a nucleotide, or the presence of still some other inherited disease of the fetus. Of course, the genetic characteristics may also reveal that the fetus is normal. Finally, a diagnostic readout is provided for the mother and/or the fetus.

For oncological testing, the genetic traits may indicate the presence of a particular genetic mutation, or a cancer. Of course, the genetic characteristics may reveal the absence of any such disorder from the patient. Based on the above findings, an appropriate cancer therapy or other prognostic measures may be recommended for the patient. In a similar fashion, these techniques may be used for diagnostic applications related to the characterization of rare immune cells, or auto-immune diseases, or organ transplant rejection.

The invention admits of its applicability to other diagnostic disciplines besides NIPT and oncology. Clearly, the techniques and methods of the invention find many advantageous embodiments. The details of the invention, including its preferred embodiments, are presented in the below detailed description with reference to the appended drawing figures.

BRIEF DESCRIPTION OF THE DRAWING FIGURES

FIG. 1 shows an exemplary workflow for non-invasive genetic testing based on cell-based diagnostics, according to the present invention.

FIG. 2A-B show a comparison of the testing protocols of the traditional cell-free DNA (cfDNA) based detection of fetal abnormalities (trisomy), and cell-based diagnostics using cell isolation by limiting dilution, according to the teachings of the present invention.

DETAILED DESCRIPTION

The figures and the following description relate to preferred embodiments of the present invention by way of illustration only. It should be noted that from the following discussion, alternative embodiments of the structures and methods disclosed herein will be readily recognized as viable alternatives that may be employed without departing from the principles of the claimed invention.

Reference will now be made in detail to several embodiments of the present invention(s), examples of which are illustrated in the accompanying figures. It is noted that wherever practicable, similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

Figure 1:
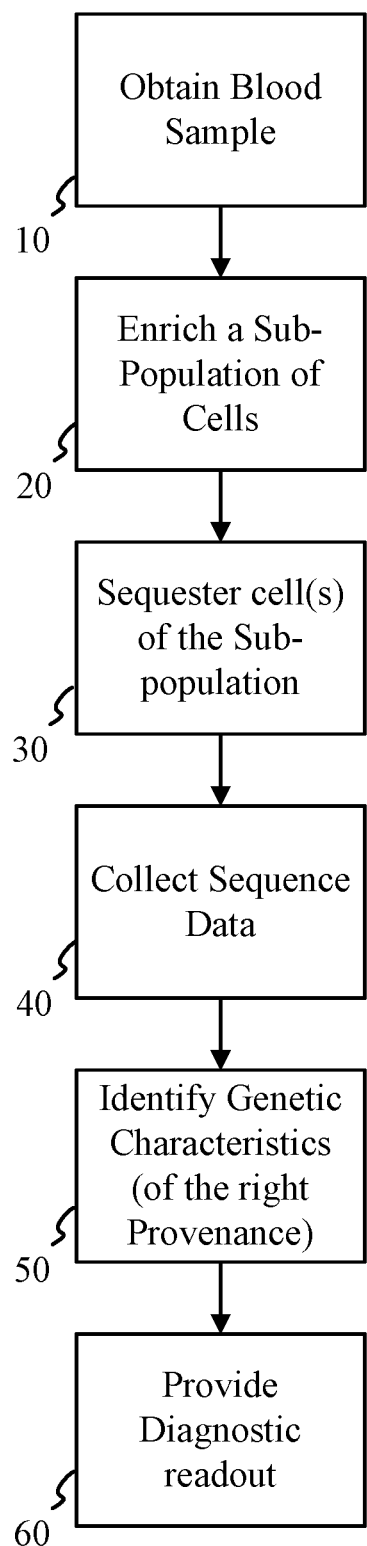

The various aspects of the invention will be best understood by initially referring to the exemplary workflow presented in FIG. 1 embodying the main aspects of the invention. According to the diagnostic techniques of the invention, a blood sample is first obtained from a patient—step 10. Then a specific sub-population of cells in the blood sample is enriched—step 20. Cells of the sub-population are then isolated or sequestered into individual cells or groups of cells—step 30. The isolated cell(s) is/are then sequenced—step 40. Sequencing is typically performed after first performing any necessary nucleic acid amplification.

The sequence data thus obtained is then analyzed for genetic characteristics/traits related to a particular condition or disease/disorder—step 50. Finally a diagnostic readout is provided—step 60. Importantly, the analysis/diagnosis is carried out only for the cells of the correct provenance, so that the number of false positives in the diagnostic readout is significantly reduced. This is possible because as a part of the analysis of the sequence data of the cells, the provenance of the cells of the sub-population is determined, and thus the diagnosis is carried out only for the cells of the correct type of provenance.

The techniques presented above are particularly suited for performing non-invasive prenatal tests (NIPT), as well as for performing non-invasive tests in oncology, transplant rejection, auto-immune disease, and rare immune cell characterization. Explained further, the blood sample from an expecting mother or an oncology patient may be analyzed using the above process. In such an analysis, circulating fetal cells (CFCs) or circulating tumor cells (CTCs) in the blood sample are analyzed for the diagnosis of birth defects in the fetus or the presence of cancer. The process is further illustrated in the diagram of FIG. 2A-B in the context of NIPT, against comparison with the traditional methods.

Figure 2A:
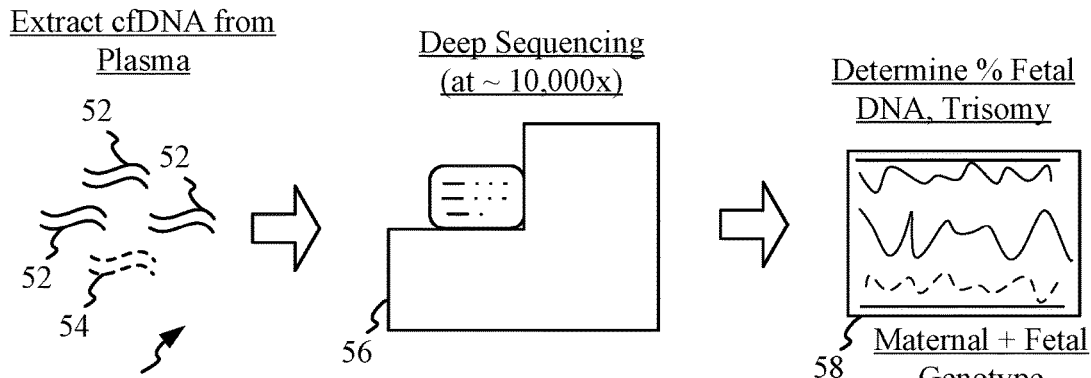

Specifically, in FIG. 2A representative of cell-free DNA (cfDNA) based analysis of the prior art, cfDNA is extracted from the plasma of the blood of the patient (expecting mother in the case of NIPT). cfDNA sample thus obtained, consists of the cfDNA of maternal origin shown by reference numerals 52 as well as the fetal cell-free DNA (fcfDNA) of fetal origin—also sometimes referred to as cell-free fetal DNA (cffDNA), shown by reference numeral 54 and represented by the dashed lines of chromosomal shapes.

The combined maternal and fetal cell-free DNA is then sequenced by a DNA Sequencer 56, which is then followed by a diagnostic analysis phase 58. Diagnostic analysis 58 of the prior art is based on the sequencing of the entire blood sample, consisting of both cfDNA and fcfDNA. The sequencing typically required to be done is at a fairly high depth, typically greater than 1,000× or greater than 10,000×. Based on the sequencing step, the proportion/percentage of the cells of fetal DNA are estimated in the cfDNA sample.

Then based on this percentage, a diagnostic evaluation of the fetal DNA is provided which may include an indication of the presence of an aneuploidy in the fetal DNA. This technique of the prior art is prone to a high number of false positives. In other words, the diagnostic evaluation only serves as a screening test that needs to be followed by usually invasive confirmatory test(s).

Figure 2B:
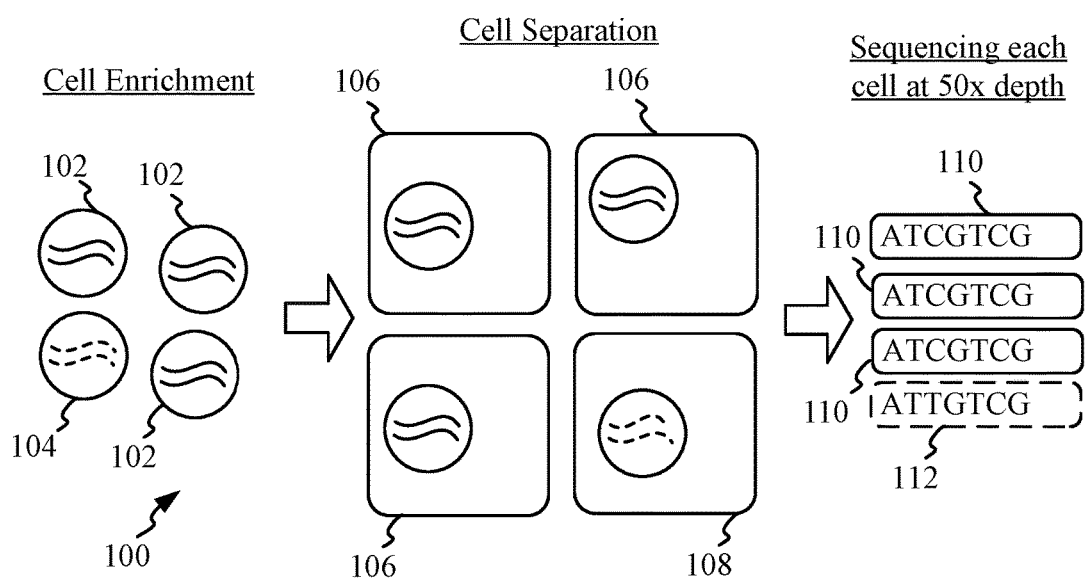

In contrast, as shown in FIG. 2B representative of the cell-based diagnostic evaluation techniques of the present invention, fetal cells in the blood sample of the mother are first enriched. The blood sample with enriched sub-population of fetal cells is shown as a collection of the individual cells of the mother 102, and those of the fetus 104. In particular, three such maternal cells are shown by reference numerals 102 and one fetal cell is shown by the reference numeral 104 in FIG. 2B.

The step of cell enrichment is followed by cell separation or sequestration as mentioned above. During this step, individual cells or groups of cells are separated or sequestered. After cell separation, the population of fetal cells analyzed may be further enriched by only analyzing cells that have a higher probability of being fetal as determined by either morphological factors, immunohistochemistry or staining of specific proteins expressed by the target fetal cells.

FIG. 2B shows three wells 106 containing maternal cells 102, and one well 108 containing a fetal cell 104. After sequestration, cell sequencing can commence as shown in FIG. 2B. Because each sequence originates with a single DNA strand per cell, each cell sample according to the invention may be sequenced at a relatively low depth (i.e. of the order of 50×). The low-depth sequencing is usually accompanied by a consensus operation to determine the correct provenance of the cells as will be further explained below.

This is a major advantage over the techniques of the prior art that require cfDNA samples to be sequenced at depths greater than 1,000× or 10,000×. However, it is worth noting that with many more single cell sequencing samples, the overall number of reads would typically be comparable and thus the sequencing cost is likely to be on parity as compared to traditional techniques. Nonetheless, the invention admits of having this differentiation potentially leading to reduction in diagnostic costs with the use of appropriate technological means and devices.

The fetal sequence obtained above is shown by the dashed box 112 in FIG. 2B, while the maternal sequences are shown by solid boxes 110. As already mentioned above, the present techniques allow for a much lower false positive rates in the diagnostic readout than otherwise possible by the techniques of the prior art (FIG. 2A). Thus such a test can serve as a screening and a confirmatory test, without necessarily requiring a follow-up confirmatory, and usually invasive, test as in the currently available testing modalities of the prior art.

Having explained the basic operation of the diagnostic system and methods of the invention, let us know return our attention to the workflow/protocol of FIG. 1, and look at steps 20-60 of that workflow in much more detail.

Enrichment:

Although the invention admits of any cell enrichment techniques that may be employed in the workflow of FIG. 1, of particular interest are immunomagnetic separation, used preferably in conjunction with antibody binding markers and cell morphology based separation criteria such as cell size, cell deformability/elasticity, dielectrophoresis, inertial forces and shear forces, etc. According to the invention, these methods may be used singly or in combination. But first let us provide a brief introduction to microfluidics, as its various structures and devices are utilized by various aspects of the present invention.

Microfluidics is a multidisciplinary field with applications in many industries including biotechnology. It is the field of study where low volumes of fluids are processed for cell manipulation, multiplexing, high-throughput screening and automation. Microfluidic systems have shown unique advantages in performing functions such as controlled transportation, immobilization, and manipulation of cells, as well as separation, mixing, and dilution of chemical reagents, which enables the analysis of intracellular parameters, even on a single-cell level.

The present invention applies the above benefits of microfluidics in its various embodiments. Specifically, in one embodiment, the enrichment process may use immunomagnetic separation. Immunomagnetic separation (IMS) methods are based on the attachment of small magnetizable particles/beads to cells via antibodies or lectins. When the mixed population of cells is placed in the influence of a magnetic field, those cells that have beads attached are attracted/repelled to/from the magnet and may thus be separated from the unlabeled cells.

Thus the enrichment process as employed in the invention may utilize one or more cell markers to which magnetic beads may be attached, and then positive and negative fractions of the mixed cell population can be sorted utilizing a magnetic field. This may be accomplished while utilizing a variety of microfluidic devices. The principles and workings of these techniques are well understood in the art and will not be delved into detail in this specification. Briefly, magnetic beads are functionalized to bind different cell populations. In one instance, beads may be pre-conjugated with one or more antibodies to specific proteins, such that the conjugated beads recognize and bind preferentially to cells expressing antigens to said antibodies. These are then brought into contact with the starting cell population, whereby only a subset of cells bind with the beads. This is referred to as the direct binding method.

Alternatively, in what is called the indirect binding method, antibodies with a linker molecule (like biotin or immunoglobulin) are first added to the cell suspension and bind the antigen. The cells are then exposed to beads coated with the complementary linker molecule (like streptavidin) in order to bind beads to cells expressing the antigen of interest. The cell mixture is then exposed to a magnetic field either inside a cavity, or while flowing across a field inside a capillary or microfluidic channel. In this manner, bead decorated cells are separated from the rest of the suspension (i.e. from cells that do not express the antigen of interest).

In another embodiment, the enrichment process may use one of the various cell morphology or physical property criteria such as cell size, shape, elasticity/deformability, inertial forces, or dielectric constants. These techniques can also be typically used in conjunction with various microfluidic devices. The principles and workings of these techniques are also well understood in the art and will not be delved into detail in this specification. Generally a cell mixture is introduced into a separation cavity, which may be a microfluidic channel, and is then subjected to forces that discriminate between cell populations based on physical properties. Examples include size exclusion, inertial forces under flow, and shear forces. The separated populations are then collected either by traditional fluid handling (i.e. pipetting) or by directing flow of the different populations into different microfluidic channel outlets, or a combination of the above.

Other embodiments use any antibody binding characteristics of the cells in the blood sample as markers to be exploited during cell enrichment. Still other embodiments may use any other techniques known to a person of average skill in the art in the enrichment step of FIG. 1, including Fluorescence Activated Cell Sorting (FACS). As already stated, all the above techniques during the step of enrichment may be used singly or any in combination to achieve the desired level of purity of the enriched cell population.

The desired level of purity should be at least 1% but ideally 10% or more of fetal cells against a background of maternal cells for NIPT diagnostics. Similarly, the desired level of purity should be at least 1% but ideally 10% or more of tumor or other types of diseased cells against a background of normal cells for oncological or other diagnostics.

Now let us return to the workflow of FIG. 1 and consider the next step 30 of cell sequestration/separation in much more detail.

Cell Sequestration:

After enriching the cells of a sub-population of interest, such as fetal cells for NIPT procedures and cancer cells for oncology procedures, individual cells or groups of cells of the sub-population are separated/sequestered. The present invention takes advantage of the various possible modalities of cell sequestration.

In one variation, single cell separation/sequestration may be performed by Limiting Dilution into wells preferably aimed at dispensing one cell per well of a well plate as shown in FIG. 2B. This step results in a statistical distribution of mostly 0, 1, or 2 cells per well. Alternatively, a FACS system may be use to both enrich the desired cell population (as mentioned in the above section), and to dispense single cells per well.

Additionally, a variety of microfluidic architectures and devices may be used. One such microfluidic architecture utilized in a preferred embodiment uses single cells that get trapped at the junction of small and large microfluidic channels.

After cell trapping, the sub-population of target cells (e.g. fetal cells for NIPT, and cancer cells for oncology) that are analyzed may be further enriched by only analyzing cells that have a higher probability of being the target cells as determined by either morphological factors, immunohistochemistry or staining of specific proteins expressed by the target cells. The cells are then lysed with an appropriate lysing agent, and then the contents of each lysed cell are passed into a separate reservoir. This process is illustrated in the microfluidic apparatus 200 and its associated methods of FIG. 3A according to the invention.

Figure 3A:
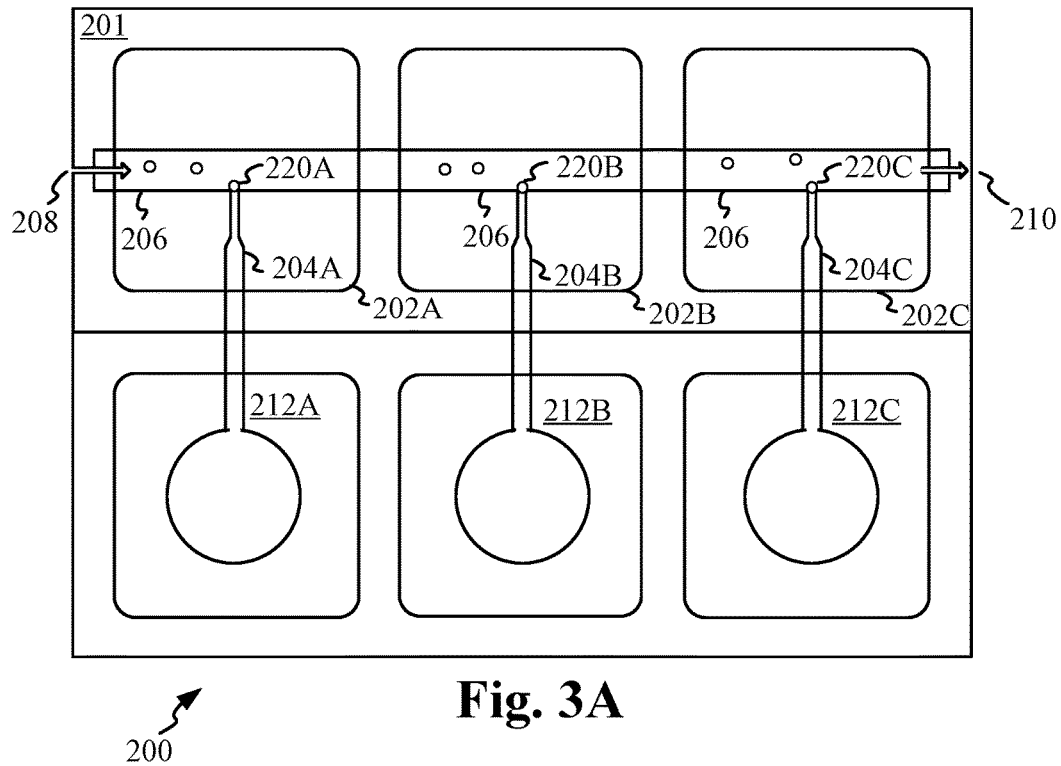
FIG. 3A shows cell immobilization at microfluidic channel junctions, specifically, single cells trapped at junctions and lysed by introducing a buffer such that cellular contents end up in secondary wells.

FIG. 3A shows a view of microfluidic apparatus 200 as seen from the top looking down, or from the bottom looking up. The figure shows a large microfluidic channel 206, connected with a smaller microfluidic channel 204A. Microfluidic channel 206 contains an enriched cell suspension obtained after the enrichment process described above. Individual cells in the cell suspension in channel 206 are shown by small circles. According to the invention, a pressure differential between the smaller microfluidic channel 204A and larger microfluidic channel 206 results in individual cells in the suspension to get trapped at the junction of microfluidic channels 206 and 204A. A cell 220A trapped at the junction of channels 206 and 204A is shown in FIG. 3.

The same setup is replicated thrice in the arrangement shown in FIG. 3A with corresponding elements 204B-C, 220B-C indicated, and channel 206 extending across all three. However, where convenient in the below explanation, we may facilitate the discussion by employing only the first portion of the above scheme, with the knowledge that same/similar processes occur in the other replicated portions, and will draw attention to any differences if and when necessary.

Figure 3B:
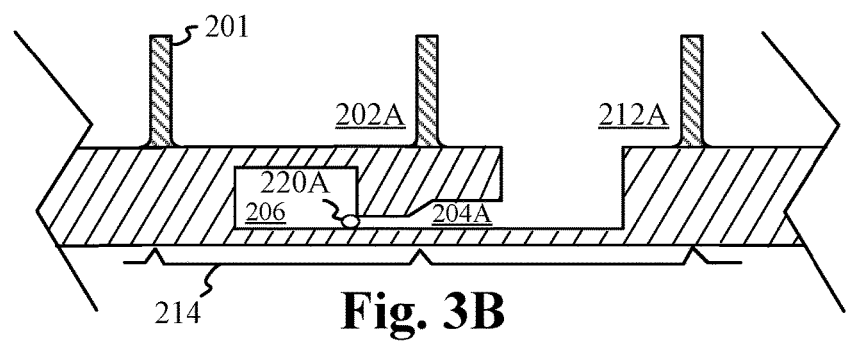
FIG. 3B shows a cross-sectional view of one portion of the microfluidic architecture for the embodiment of FIG. 3A.

To facilitate understanding, FIG. 3B further shows a cross-sectional view of the first portion of apparatus 200. Cell 220A is seen trapped in FIG. 3A-B at the junction of channels 206 and 204A and is thus immobilized. Such trapping/immobilization will occur under the influence of a negative pressure in channel 204A. In other words, and as will be apparent to skilled artisans familiar with an intuitive application of the basic laws of physics and fluid dynamics, if a negative pressure differential between channel 204A and channel 206 is created, that will encourage cells in the solution carried by channel 206 to be trapped at its junctions with smaller channel 204A.

As already mentioned, after cell trapping, the sub-population of target cells (e.g. fetal cells for NIPT, and cancer cells for oncology) that are analyzed may be further enriched by only analyzing cells that have a higher probability of being the target cells as determined by either morphological factors, immunohistochemistry or staining of specific proteins expressed by the target cells. Specifically, cells that are determined to be of non-target origin (e.g. maternal cells for NIPT, and normal cells for oncology), may be removed from the traps by applying positive pressure to wells 212A-C, in cases where imaging determines cells 220A-C to be likely of non-target origin. In this way, cell trapping and selective release may be used to enrich a certain rare cell population.

At this stage, a lysing agent/buffer can be introduced in microfluidic channel 206 at an inflow 208 and exited at an outflow 210. The lysing agent will lyse cells 220A, 220B, 220C and their lysed contents will then travel under the applied pressure and be deposited in separate reservoirs 212A, 212B and 212C respectively.

The pressure differential between channels 206 and 204A as described above, can be easily created by pressing a mating surface from the top against the upper structure of well plate 201. As shown in FIG. 3A-B, each channel junction of channels 206 and 204A-C is surrounded by the walls of reservoirs 202A-C in the shape of squares with rounded corners. An exemplary structure is that of a Society for Biomolecular Screening (SBS) format well plate with a rigid upper structure formed of injection molded plastic.

When an appropriate surface with interfaces mating to this rigid upper structure is pressed against it, this results in pressure applied to channels 204A-C and consequently to the inputs of reservoirs/wells 212A-C. It is under the influence of this pressure that cell trapping occurs as described above. Additionally, inflow 208 and outflow 210 may in turn be connected to input and output wells of the same upper structure (not shown) for ingress or egress of various fluids, including lysing buffer. Additionally, any other appropriate mechanisms known to those skilled in the art may be used to cause negative pressure in the desired channel(s), e.g. by using a syringe for suction.

In summary, pressure manipulation in various channels of FIG. 3A-B may be achieved by pressing a sheet/substrate of glass or some other suitable material as needed against the microfluidic structures from above or below. One such pressing substrate 214 is shown in the cross-sectional view of FIG. 3B. Notice that when pressing substrate 214 is pressed upwards, the three protrusions in pressing substrate 214 will press against the various microfluidic channels, thereby increasing the flow resistance or entirely cutting it off. Specifically, as shown in FIG. 3B, once cell 220A has been lysed and its contents have deposited in reservoir/well 212A, pressing substrate 214 may be pushed upwards to cut off flow in channel 204A thereby ensuring that lysed contents of cell 220A in well 212A are not contaminated. Such a technique is also referred to as a "foot on the hose valve-ing" technique.

In a similar fashion, and advantageously, after the introduction of the lysing agent in channel 206, each of trapped/immobilized cells 220A-C are kept separate from each other by having an increased flow resistance in channel 206 between each of its junctions with channels 204A-C of the three replicated portions shown in FIG. 3A. This can be accomplished by pressing a sheet/substrate of glass or some other suitable material against channel 206 from below to reduce or cut-off flow selectively.

In one embodiment, this is accomplished as follows. Notice three reservoirs indicated by reference numerals 202A, 202B and 202C in the replicated architecture on a well plate 201 shown in FIG. 3A. Each reservoir 202A, 202B, 202C has a familiar outline as shown by the squares with rounded corners. Analogously to the foot-on-the hose valving scenario for channel 204A described above in reference to FIG. 3B, pressing substrate 214 may have protrusions to cut off flow in channel 206 at its intersections with the left and right edges of reservoirs 202A-C and also to cut off flow in channels 204A-C at their intersections with the lower edges of reservoirs 202A-C. Such an exemplary pressing substrate 214 is further shown in a three dimensional side view in FIG. 3C, which has protrusions in the shape of two squares 215A and 215B that when pressed against two reservoirs, will cut off flow entirely around them.

Once the lysed contents of cells 220A-C have been deposited and secured in reservoirs/wells 212A-C, sequencing and analysis can begin as will be further taught below. Note that wells 212A-C are again reminiscent of a standard well plate as will be observed by the skilled reader. Such a design facilitates integration of this process with standard fluid handling and/or Quantitative Polymerase Chain Reaction (qPCR) equipment. The architecture shown in FIG. 3 also has the advantage of having minimal cross-contamination ("cross-talk") due to diffusion between different reservoirs 212A, 212B and 212C.

The above scheme can be used to sequester contents of individual cells 220A-C or of multiple cells from the enriched suspension of cells in channels 206. Multiple cells may be trapped and lysed from the enriched suspension with their contents stored in reservoirs 212A-C. This may be accomplished by repeating the application of negative pressure after a cell 220A, 220B, 220C has been trapped and lysed, so that the same process can be repeated for additional cells of the enriched suspension.

Another embodiment of the invention uses cell trapping at channel junction residing inside or at the bottom of the wells of a standard well plate. In such a scenario a smaller microfluidic channel connects to a well at a junction where the cell trapping happens. This scenario is illustrated in the microfluidic apparatus 250 and its associated methods of FIG. 4A, according to the invention.

Figure 4A:
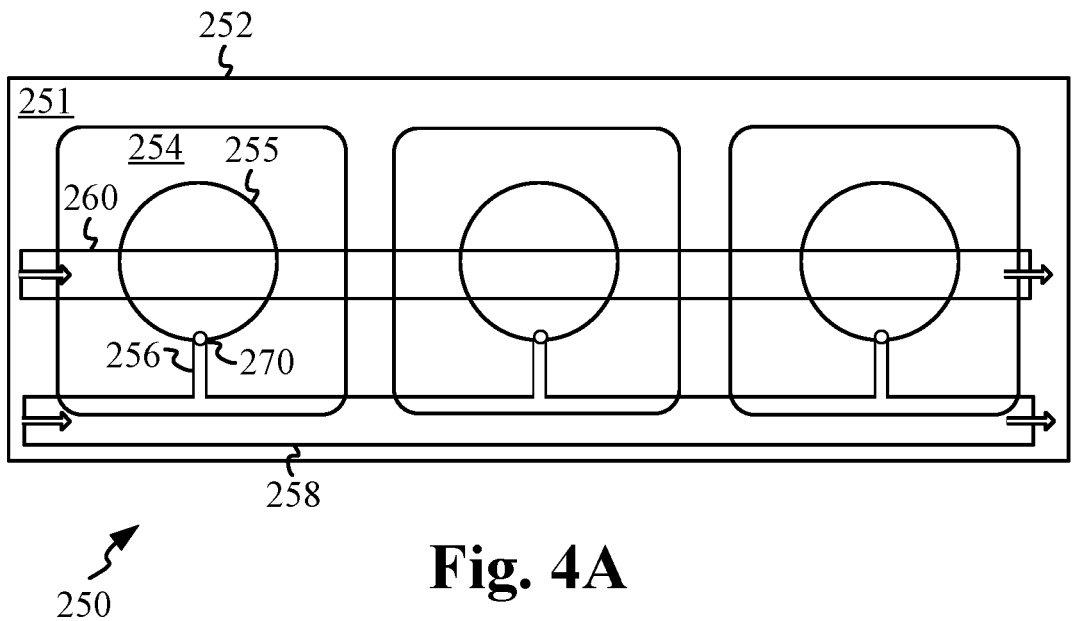
FIG. 4A shows a variation where a microfluidic channel delivers the cell suspension directly to the wells where trapping happens. Cells are then lysed by adding lysis buffer to the wells either by pipetting, or via another microfluidic channel.

FIG. 4A shows a microfluidic channel 260 feeding a reservoir 254 having a well 255 caused by a punch-hole in reservoir 254. Notice that in contrast to the embodiment of FIG. 3A, here we are drawing a distinction between the surrounding reservoir and the actual well in it caused by a punch-hole, and where the channel junction resides. Reservoir 254 and well 255 are a part of a standard well plate, a section 252 of which is shown. Enriched cell solution is fed from channel 260 to reservoir 254.

Under the influence of a negative pressure, as in the embodiment of FIG. 3, cell trapping occurs inside well 255 at its bottom with its junction to a smaller channel 256. Specifically, a cell 270 is being shown trapped at the intersection of well 255 and channel 256. Note that the same scheme is replicated in FIG. 4A, however repeating reference numerals have been omitting from the drawing and the associated explanation for clarity and to avoid undue repetition. To facilitate understanding, FIG. 4B further shows a cross-sectional view of the first portion of apparatus 250.

Figure 3C:
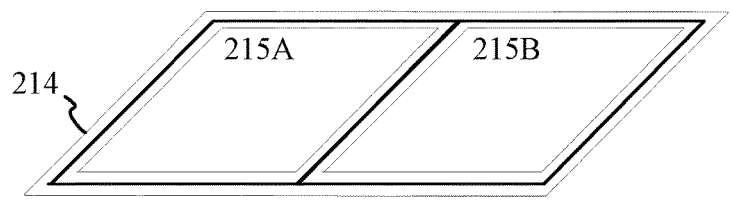
FIG. 3C shows a three dimensional side view of an exemplary pressing substrate for the embodiment of FIG. 3A-B.
Figure 4B:
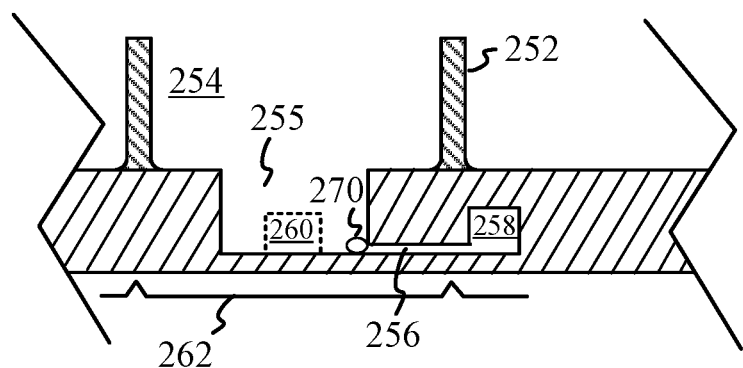
FIG. 4B shows a cross-sectional view of one portion of the microfluidic architecture of FIG. 4A.

As with the embodiment of FIG. 3A-C, after cell trapping, the population of fetal cells (or cells of interest) analyzed may be further enriched by only analyzing cells that have a higher probability of being the target cells, as determined by either morphological factors, immunohistochemistry or staining of specific proteins expressed by target cells. Cells that are determined to be of non-target origin may be removed from the traps under pressure. Referring to FIG. 4A-B, if imaging determines cell 270 to be of likely non-target origin, then it may be removed by applying negative pressure to reservoir 254. In this way, cell trapping and selective release may be used to enrich a certain rare cell population prior to lysis.

Once cell 270 is trapped and immobilized, a lysing buffer/solution, followed by a DNA amplification solution or other agents/reagents as desired, can be added directly to reservoir 254 by a pipette. Alternatively, the lysing buffer/solution can be added via another microfluidic channel carrying the solution directly to wells 255. Such a channel 258 for carrying lysing and other/or solutions is shown in FIG. 4A-B and is connected to reservoir 254 at punch-hole/well 255 via a small channel 256.

Note that after lysing, channel 258 may be reused for carrying other agents/reagents, such as eluting and DNA amplification solutions, for example. Preferably, these reagents may be first carried by a main channel 251 which in turn may be fed by other feeding wells (not shown) that are selectively activated/pressurized as and when desired to feed the above mentioned agents/reagents into reservoir 254. In an exemplary scenario, main channel 251 will feed channel 258 that will in turn feed reservoir 254.

A person skilled in the art will recognize the vast variety of microfluidic designs and options available to practice the principles and teachings taught herein. The architecture shown in FIG. 4A-B also has the advantage of having a minimum cross-contamination ("cross-talk") due to diffusion between different reservoirs 254 and wells 255.

Furthermore, and similarly to the architecture of FIG. 3, the architecture in FIG. 4 can be fully or partially influenced/covered by a sheet/substrate of glass or some other suitable material as needed to manipulate pressure, under the influence of which cell trapping at wells 255 occurs, or to manipulate flow in various channels as desired. FIG. 4B shows an exemplary pressing substrate 262 which when pressed up against the microfluidic structures above, will cut off flow in channel 256 so that the lysed contents of cell 270 in well 255 stay secure.

As in the earlier embodiment, the above scheme can be used to sequester contents of an individual cell 270 or of multiple such cells from the enriched cell solution. In either of the above techniques of cell sequestration, typically a group or subset of cells ranging from 1 to 500 cells may be sequestered for further analysis.

Another variation uses Limiting Dilution Analysis for cell sequestration. Those skilled in the art will understand that Limiting Dilution Analysis is a technique in cell biology for estimating the frequency of a specific type of cell in a complex mixture of cells. This type of cell may be identified by its response to an activation signal. The activation signal can induce cell proliferation, differentiation, or the expression of specific cellular functions in the responder cells, which may include cytotoxic activity or the release of cytokines or antibodies. As already described earlier, in this variation, single cell separation/sequestration may be performed by Limiting Dilution into wells meant to preferably dispense one cell per well of a well plate as shown in FIG. 2B. This step typically results in a statistical distribution of mostly 0, 1, or 2 cells per well.

Still another variation employs Fluorescence Activated Cell Sorting (FACS) for cell separation/sequestration. FACS provides a technique for sorting a heterogeneous mixture of cells into two or more containers, one cell at a time. This sorting is based upon the specific light scattering and fluorescent characteristics of each cell. Both the above variations may also employ the benefits of appropriate microfluidic systems and architectures to achieve their desired objectives of cell sequestration, and obtain individual cells or a group of cells of a sub-population of interest into isolated reservoirs/wells for further analysis.

Now let us return to the workflow/protocol of FIG. 1 and consider the next steps of 40, 50 and 60 of cell sequencing, analysis and diagnosis in much more detail.

Cell Sequencing and Genetic Analysis:

According to the above teachings, the contents of individual cells or a group of cells of a sub-population of interest can be saved in reservoirs/wells. The cells of interest comprising the sub-population can be of fetal origin for NIPT diagnostics, or they can be tumor cells for oncological diagnosis, or they can belong to another disease or disorder for the appropriate diagnosis.

At this point, any necessary nucleic acid amplification may be carried out to the cell populations in the reservoirs/well. The invention is agnostic of such amplification methods available in the art. A non-exhaustive list of such methods is Polymerase Chain Reaction (PCR), Ligase Chain Reaction (LCR), Loop Mediated Isothermal Amplification (LAMP), Nucleic Acid Sequence Based Amplification (NASBA), Strand Displacement Amplification (SDA), Multiple Displacement Amplification (MDA), Rolling Circle Amplification (RCA), Helicase Dependent Amplification (HDA), Ramification Amplification Method (RAM), etc.

After the necessary amplification, sequencing of the cell populations in the reservoirs can begin with the intent of performing diagnosis. Preferably, prior to sequencing, a barcode is added to each cellular content in the reservoirs. Then sequencing needs to be performed only on the barcoded contents. Sequencing or genetic sequencing, maps/sequences the genetic code of the cells in the reservoirs. According to the invention, the diagnosis is based on the genetic characteristics identified in the gene sequences, and needs to be performed on the cells that were sequestered as explained above, and those which can be determined to be of the right type of provenance. Exemplary provenance types can be maternal or fetal origin in the case of NIPT, or normal or cancer origin in the case of oncological testing.

In other words, the genetic analysis to determine abnormalities needs to be performed on cellular contents of only those reservoirs/wells of FIG. 3A and FIG. 4A, that are determined to be of the correct provenance as will be further taught below. Still further explained, and referring to FIG. 3A, sequence data from all reservoirs/wells will be first analyzed to determine the provenance of the cellular contents in each reservoir/well. If for example, the cellular contents of reservoir 212B in FIG. 3B are determined to be of fetal origin in NIPT, then only the contents of reservoir 212B need to be further analyzed, and not those of reservoirs 212A and 212C.

Thus for NIPT purposes, the analyzed cells would belong to the CFCs from the blood sample of the expecting mother. The diagnostic readout in this case will be based on the features of the fetal genome detected from the sequence data, uncontaminated by maternal DNA, and may include an indication of aneuploidies, such as trisomy 8, trisomy 9, trisomy 13, trisomy 18, trisomy 21, trisomy 22, an XXX status, an XXY status, an XYY status, etc. The diagnostic readout may also include an indication of the presence of other abnormalities such as insertions and deletions of single nucleotide variants, or the presence of still other inherited diseases as indicated by the genetic sequence of the fetal cells.

Analogously, for oncological testing, the genetic analysis of the sequestered cell or group of cells needs to be performed only on the cell(s) that are known to be of cancerous origin, and hence would belong to the CTCs from the blood sample of the patient. The diagnostic readout in this case will be based on the features of the genetic mutations and the cancer genome detected from the sequence data of the tumor cells, and may include guidance on suitable therapies or other prognostic measures for the patient. The therapeutic guidance may include alterations to existing therapies or recommendations on entirely new ones. In a similar fashion, these techniques may be used for diagnostic applications related to the characterization of rare immune cells, or auto-immune diseases, or organ transplant rejection.

Now let us see how the provenance of the sequestered cells is properly ascertained prior to the above explained genetic analysis, according to the invention. For this purpose, the invention checks single nucleotide variants (SNVs) information of the cells from their sequence data. This is done for each reservoir/well i.e. 212A-C of FIG. 3A and 254/255 and their replicated counterparts of FIG. 4A. For NIPT purposes, based on the differences in SNVs and other individual-specific genetic differences between maternal and fetal cells, the provenance of the cells is ascertained. For oncological diagnosis, based on the differences in SNVs and other genetic abnormalities of tumor cells that are not present in normal cells (e.g. copy number variations, gene fusions, etc.), the provenance of the cells is ascertained. The diagnostic readout is then provided based only on the fetal cells in the former case and based only on the tumor cells in the latter case. It will be clear to the skilled reader that either DNA or RNA/gene expression may be used to determine cell provenance.

In an alternative variation, a consensus operation is employed to check the origin/provenance of each cell. In this variation, when applied to NIPT diagnostics, individual sequestered cells in each reservoir are first tagged by unique barcodes, which may be randomly generated barcodes. Then each molecular sequence is aligned to a standard/reference genome, and the results compared against each other and then clustered into sets of like cells (reservoirs displaying minimal differences).

Based on a suitable consensus cutoff, then the majority of 'like' sequences in the cluster are selected to belong to the mother (majority), and the remaining sequences are then known to belong to the fetus (minority), noting that some additional minority clusters may be contamination. NIPT genetic analysis is then performed on the molecular sequences of fetal origin, and a diagnostic readout provided as explained above.

The above determination may also benefit from techniques to reduce the errors present in the sequences of each starting molecule that is sequenced (ideally before the assignment to the maternal or fetal set is performed). In this variation, in addition to using cellular barcodes, unique molecular barcodes are attached to each starting molecule before amplification and sequencing. Thus sequences that originated from the same individual starting molecular barcode must match exactly, once errors have been eliminated. In one embodiment, error elimination may be done by an appropriate statistical approach such as outlier detection, or by one of a number of consensus operations like selecting only the alteration present in most sequences from the same molecular barcode.

Additionally, any other statistical approach may also be employed to determine consensus amongst the sequences and to eliminate errors, and to consequently improve the determination of cell provenance. The advantage of the above consensus operation is that by its very nature, it serves to greatly reduce the effects of nucleic amplification and sequencing errors by requiring consensus from all sequences derived from a unique starting molecule. Another advantage of such a consensus process among different cell sequences is that the sequencing operation of the fetal cells may be carried out at much lower depths, of the order of 50×.

Still another key advantage of the apparatus and methods of the invention is that the number of false positives in the event diagnostic readout is significantly reduced. This is further illustrated in FIG. 5A and FIG. 5B, representing the effectiveness of the present invention against standard techniques for diagnosing an aneuploidy such as trisomy 21 based on mock data.

Figure 5A:
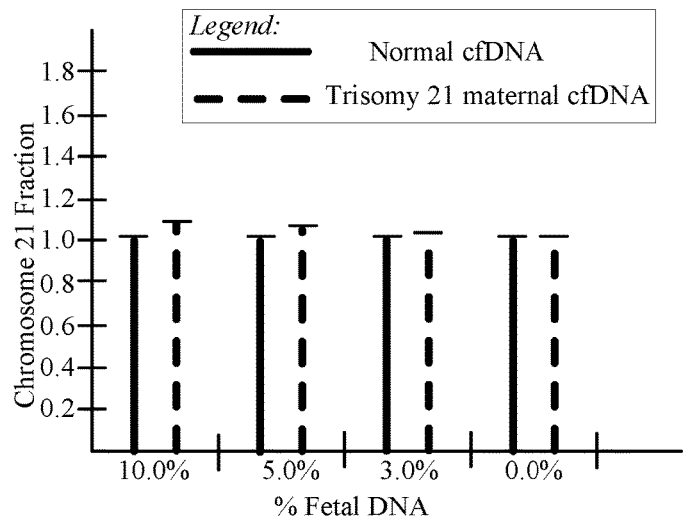
FIG. 5A shows, based on mock data, chromosome 21 copy number variation data for normal versus maternal cell-free DNA (cfDNA) using traditional techniques, where the fetus is a carrier of Trisomy 21. Fetal DNA content found physiologically is varied along the x-axis, from 10-0%.

Specifically, FIG. 5A shows mock data based on cell-free DNA (cfDNA) of a normal maternal blood sample represented by dark solid lines versus maternal blood sample where the fetus is a carrier of Trisomy 21 represented by dark dashed lines. The fetal DNA content found physiologically is varied along the x-axis, from concentrations of 10% to 0%. As fetal DNA concentration is changed from: 10% to 5% to 3% to 0%, the corresponding change as compared to normal in the number of chromosome 21 copies in maternal cfDNA sample where the fetus is the carrier of Trisomy 21 is: 1/20=5% to 0.5/20=2.5% to 0.3/20=1.5% to 0/20=0% respectively. This is amply illustrated by the minute change in length of the dashed lines from left to right with the corresponding change in fetal DNA content in FIG. 5A. Note that at 10% concentration, the fetal DNA content (3 copies of chromosome 21) would be 3/20=15%.

Figure 5B:
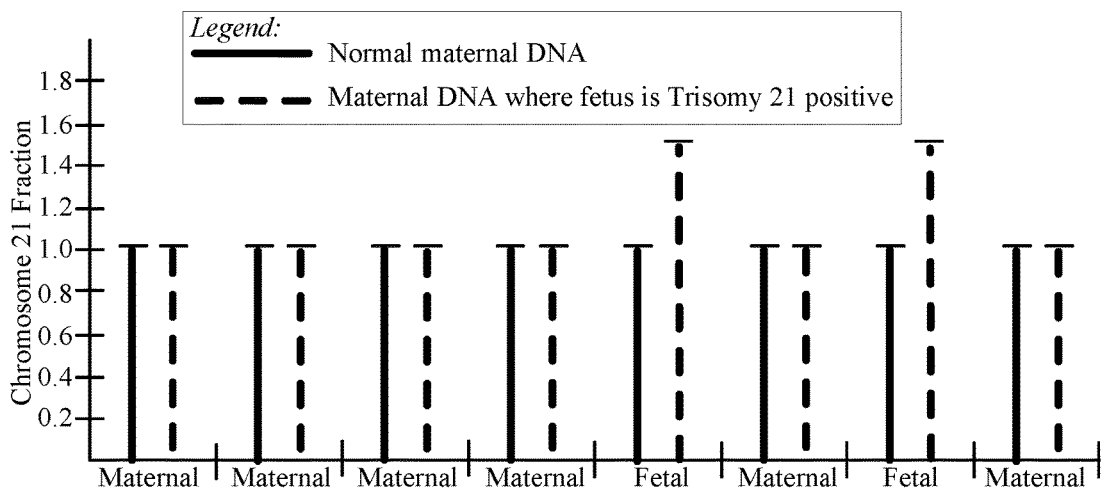
FIG. 5B shows, based on mock data, chromosome 21 copy number variation data based on cell-based sequences of normal maternal cells versus maternal cells where the fetus is a carrier of Trisomy 21, according to the invention.

In contrast, in FIG. 5B representative of the cell-based non-invasive diagnostic techniques of the instant invention, normalized chromosome 21 readouts of single cell sequences of normal maternal cells versus maternal cells where the fetus is a carrier of Trisomy 21 are shown as solid and dashed dark lines respectively. The diagram illustrates the spike in the chromosome 21 readout for fetal cells against normal maternal cells. The provenance of each cell read is indicated below the x-axis in FIG. 5B. Obviously the normalized maternal readout is 1.0 for the number of chromosome 21 copies, corresponding to 2 such chromosome 21 copies in the maternal cells—same as normal. However, the normalized fetal readout is 1.5, corresponding to 3 such chromosome copies in the fetal cells with the trisomy—50% more than normal.

That is a difference in the signal of 50% as compared to 5% cfDNA measurements (also see FIG. 5A), a significant confirmatory difference against the traditional non-invasive analysis of cfDNA shown in FIG. 5A. Unsurprisingly, the resultant signal-to-noise ratio (SNR) is also much better than the traditional techniques. The noise level in cell-free techniques is likely to be 5% versus 5-10% using the cell-based techniques of the instant invention because of the lowered sequencing depth of coverage as explained above.

Thus the SNR of the present invention is likely be in the range of 50%/10%-50%/5%=5-10 versus 5%/5%=1. That is an improvement in SNR of 500-1000% over the techniques of the prior art. The gain in SNR results in much better sensitivity/specificity in pre-natal non-invasive tests, translating into a much better positive predictive value (PPV). This further gives the present techniques the ability to assay new fetal genomic characteristics/traits like SNV related disorders.

Still in other variations, single cell immobilization using microfluidic devices explained above (see FIG. 3A-C, and FIG. 4A-B and the associated explanation) may be followed by staining of the immobilized cells. The stained cells can then be microscopically analyzed for detection of chromosome abnormalities for each individual cell. This method has the potential of lowering the cost while maintaining a high PPV of the tests as described above.

In view of the above teaching, a person skilled in the art will recognize that the teachings and methods of present invention can be embodied in many different ways in addition to those described without departing from the principles of the invention. Therefore, the scope of the invention should be judged in view of the appended claims and their legal equivalents.

We claim:

1. A cell-based 1 diagnostic method, comprising the steps of:
   (a) enriching a sub-population of cells of a blood sample;
   (b) sequestering one or more cells of said blood sample by trapping said one or more cells under negative pressure at a junction between an inside of a well and a microfluidic channel, and thereafter lysinq said one or more cells by introducing a lysing agent in said well;
   (c) sequencing said one or more cells;
   (d) determining a provenance of said one or more cells based on said sequencing;
   (e) determining a genetic characteristic of said one or more cells based on said sequencing and said provenance; and
   (f) providing a diagnosis based on said genetic characteristic.

2. The cell-based diagnostic method of claim 1, further utilizing at least one element selected from the group consisting of an immunomagnetic separation, a microfluidic manipulation, a cell morphology based separation and an antibody binding based separation, in said step (a) of enriching.

3. The cell-based diagnostic method of claim 2, further utilizing at least one cell attribute selected from the group consisting of a size, a shape, a structure, a form and an elasticity, when utilizing said cell morphology based separation.

4. A method of sequestering of cells comprising the steps of:
   (a) enriching a sub-population of said cells from a blood sample and feeding said sub population via a microfluidic channel into a reservoir; and
   (b) sequestering one or more cells of said sub-population by trapping said one or more cells under negative pressure at a junction between an inside of a well caused by a punch-hole in said reservoir and another microfluidic channel and thereafter lysing said one or more cells by introducing a lysing agent in said well.

* * * * *